United States Patent [19]

Stapp

[11] 3,956,407

[45] May 11, 1976

[54] ALKENOL PRODUCTION

[75] Inventor: Paul R. Stapp, Bartlesville, Okla.

[73] Assignee: Phillips Petroleum Company, Bartlesville, Okla.

[22] Filed: May 29, 1974

[21] Appl. No.: 474,254

[52] U.S. Cl. .......................... 260/638 R; 252/463; 260/340.7; 260/464; 260/465.9; 260/491; 260/497 R; 260/611 R; 260/614 A; 260/633; 260/617 R; 260/617 M; 260/618 R; 260/681; 260/683 R; 260/643 R

[51] Int. Cl.² .................. C07C 27/00; C07C 29/00

[58] Field of Search ........ 260/638 R, 617 R, 617 M

[56] References Cited
UNITED STATES PATENTS 3,081,357  3/1963  Alderson et al. ............... 260/638 R
3,706,809  12/1972  Moroe et al. ................... 260/638 R

FOREIGN PATENTS OR APPLICATIONS 1,228,991  4/1971  United Kingdom ............ 260/638 R
545,191  5/1942  United Kingdom ............ 260/638 R

*Primary Examiner*—Joseph E. Evans

[57] ABSTRACT

Alkenols are produced in good yields by reacting olefinic compounds with formaldehyde in an aromatic reaction diluent containing bromine- or iodine-containing catalysts. In accordance with one embodiment, alk-3-en-1-ols are produced in good yields from isobutylene and formaldehyde by carrying out the reaction in an aromatic diluent containing at least one bromine- or iodine-containing catalyst.

15 Claims, No Drawings

ALKENOL PRODUCTION

This invention relates to an improved process for the production of alkenols. In accordance with another aspect, this invention relates to an improved process for producing increased yields of alkenols by the reaction of olefinic compounds with formaldehyde in the presence of selected halogen catalysts and selected aromatic diluents. In accordance with another aspect, this invention relates to use of selected aromatic diluents for the production of alkenols from formaldehyde and olefinic compounds. In accordance with another aspect, alkenols are produced from olefins and formaldehyde in the presence of aromatic reaction diluents containing bromine- and iodine-containing catalysts. In accordance with still another aspect, alk-3-en-1-ols are produced by the reaction of isobutylene with formaldehyde in selected aromatic diluents containing at least one bromine- or iodine-containing catalyst.

The reaction of olefins with formaldehyde is known. Various expedients have been advanced to improve the yield of desired products or to alter the reaction to produce other more useful products. In accordance with the invention, it has been found that alkenols can be produced in good yields from the reaction of olefinic compounds with formaldehyde in selected aromatic diluents containing selected halogen catalysts.

Accordingly, an object of this invention is to provide an improved process for the production of alkenols.

Another object of this invention is to provide novel catalysts for increasing the yields of alkenols.

A further object of this invention is to provide novel diluents for the production of alkenols.

Another object of this invention is to provide an economically feasible process for the production of alkenols whereby high yields of desired product are obtained.

Other objects and aspects, as well as the several advantages of the invention, are apparent upon a study of this disclosure and the appended claims.

In accordance with the invention, a process is provided for the production of alkenols by contacting olefinic reactants with formaldehyde in an aromatic reaction diluent containing at least one of a bromine- or iodine-containing catalyst.

In accordance with one specific embodiment, it has been found that alk-3-en-1-ols are obtained in high yields by reacting an olefin such as isobutylene with formaldehyde under liquid phase conditions in an aromatic reaction diluent containing at least one of a bromine- or iodine-containing catalyst.

In accordance with a further specific embodiment of the invention, 3-methyl-3-buten-1-ol is produced by the reaction of isobutylene with formaldehyde in the presence of benzene, diphenyl ether, and anisole as reaction diluents and bromine- and iodine-containing catalysts as defined herein.

Olefinic compounds which are suitable for use in the instant invention are those having at least one allylic hydrogen, i.e., having the basic structure

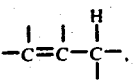

and from 3 to 20 carbon atoms per molecule. The olefinic double bond in said compounds can be part of a carbocyclic ring. Furthermore, substituents which are essentially inert under the reaction conditions can also be present in the olefinic reactant. Typical examples of such substituents include —CN, —Cl, —OCH$_3$, —CO$_2$CH$_2$CH$_3$, and the like. Of the olefinic reactants broadly suitable, the present preferred olefinic compounds are those containing only carbon and hydrogen such as the alkenes or cycloalkenes. Examples of suitable olefinic reactants include propylene, isobutylene, α-methylstyrene, 1-methyl-4-isopropenylcyclohexene, 1-methylcyclohexene, methallyl chloride, methyl isopropenyl ether, 5-methyl-5-hexenenitrile, and the like, and mixtures thereof.

Formaldehyde is employed as the aldehyde reactant in the instant invention. However, the formaldehyde reactant may be employed in any of its well-known commercially available forms such as the cyclic trimer, 1,3,5-trioxane, or the polymeric form, paraformaldehyde, and the aqueous solution (commonly called formalin) of about 37 percent concentration which can contain methanol as an inhibitor.

Catalysts suitable for use in the instant invention are selected from the group consisting of bromine, metal bromides wherein the metal is selected from Groups IA and IIA of the Periodic Table, iodine, and metal iodides wherein the metal is selected from those metallic elements with atomic numbers between 3 and 83, inclusive. The division between metals and non-metals for elements in the Periodic Table is shown, for example, in Lange's Handbook of Chemistry, revised 10th edition, pages 60, 61, McGraw-Hill, Inc., New York (1967). The bromine, metal bromide, iodine, or metal iodide may be dispersed on a conventional catalyst support material such as alumina, silica, silica-alumina, clays of various types, carbon, pumice, and the like.

Among the metal iodides, those presently preferred are the iodides of metals from Groups I and II of the Periodic Table of the Elements. Furthermore, if an alkenol is desired as the final condensation product from formaldehyde and the olefinic reactant, bromine or a metal iodide selected from Group IA of the Periodic Table are preferred. On the other hand, if a conjugated diolefin is desired as the final condensation product, a metal iodide selected from Group II or higher is preferred as the catalyst.

Examples of suitable catalysts include bromine, iodine, iodine on alumina, iodine on pumice, iodine on silica, bromine on silica, lithium iodide, sodium iodide, potassium iodide, potassium bromide, magnesium iodide, magnesium bromide, scandium triiodide, titanium tetraiodide, vanadium diiodide, molybdenum tetraiodide, manganese diiodide, ferrous iodide, iridium triiodide, nickel (II) iodide, silver iodide, cadmium iodide, lead diiodide, gallium triiodide, bismuth triiodide, aluminum iodide on silica, cobalt (II) iodide on alumina, barium iodide on silica-alumina, potassium iodide on kaolin, lithium bromide on alumina, and the like.

When the bromine, metal bromide, iodine, or metal iodide is employed on a support material as described above, the amount of bromine, metal bromide, iodine, or metal iodide present is generally from 0.05 to 5, preferably from 0.1 to 2, percent by weight of the total composition. Said compositions can be prepared by conventional methods of preparing supported catalysts. For example, a suitable support material can be treated with a solution, dispersion, or slurry of bromine, metal bromide, iodine, or metal iodide in a volatile diluent. The diluent is then evaporated to provide the supported catalyst for use in the instant invention.

The reaction of formaldehyde with an olefinic compound in the presence of the above described catalyst is also carried out in the presence of a diluent selected from compounds having from 6–20 carbon atoms per molecule and having the general formula $Ar(Z)_n$ wherein Ar is an aromatic hydrocarbyl radical whose valence is $n$, and wherein Z is a substituent selected from the group consisting of Cl— and R—O—, and where R is a hydrocarbyl radical of 1–alkyl, aryl, carbon atoms such as alkyl, cycloalkyl, and the like, and wherein $n$ can be 0, 1, or 2. It can be seen that when $n$ is 0 said diluents are aromatic hydrocarbons.

Examples of suitable diluents include benzene, toluene, cumene, chlorobenzene, m-dichlorobenzene, 1-chloronaphthalene, methoxybenzene (anisole), ethoxybenzene (phenetole), diphenyl ether, 1-methoxynaphthalene, 1,2-dimethoxybenzene, 1,3-dimethoxybenzene, 1-chloro-4-methoxybenzene, 1-chloro-3-ethoxybenzene, 4-chlorodiphenyl ether, and the like. Mixtures of the above diluents can also be employed if desired.

The temperature can be broadly from 50°–300°C and preferably from 150°–250°C. The time employed for the reaction of the instant invention can be from about 3 minutes up to 24 hours and preferably from 15 minutes to 2 hours.

The reaction of the instant invention is generally carried out under autogeneous pressure but, if desired, pressure from an inert gas such as nitrogen or helium can also be applied up to about 1000 psig of the inert gas.

The amount of catalyst (not including support material if such is employed) which is employed in the reaction of this invention is generally from 0.01 to 20, preferably from 0.05 to 10, percent by weight based on the weight of formaldehyde charged to the reaction mixture.

The molar ratio of olefinic reactant to formaldehyde for the reaction of the instant invention is broadly from 1/1 up to 20/1, preferably from 5/1 up to 13/1. However, if the olefinic reactant is especially expensive, it is within the scope of this invention to employ a molar excess of the formaldehyde to promote complete conversion of the olefinic reactant. In such instances up to about 20 mols of formaldehyde per mol of olefinic reactant can be employed.

The charge order of catalyst, formaldehyde, olefinic reactant, and diluent is not believed to be critical in the instant invention so that the above components of the reaction system can be charged to the reactor in any convenient manner.

One advantage of the process of the instant invention is that product selectivity can be varied by certain simple recovery procedures as well as by selection of the catalyst and the reaction conditions. As previously indicated, the principal product of the reaction between formaldehyde and the olefinic reactant can be an alkenol or a conjugated diolefin. For example, if isoprene is the desired end-product from the reaction of formaldehyde and isobutylene, it is preferred that the reaction mixture be fractionally distilled in the presence of the catalyst employed. The isoprene thus obtained can, of course, be subjected to further conventional purification steps if so desired. On the other hand, if 3-methyl-3-buten-1-ol is the desired end-product from the above reaction, it is preferred to remove the catalyst from the reaction mixture prior to the fractional distillation thereof. The alkenol obtained as described above can be subjected to a separate dehydration reaction using procedures taught in the art to thus provide a two-step process to conjugated diolefins obtainable in high purity. It has been found that iodine in aromatic ethers is an especially useful dehydration catalyst for the conversion of suitable alkenols to conjugated diolefins, e.g., isoprene from 3-methyl-3-buten-1-ol.

Conjugated diolefins produced according to the instant invention have important well-known uses in the art such as monomers in the preparation of rubbery or resinous polymers for tires, floor tile, containers, and the like. The alkenols have utility in several areas of the chemical arts. They may be employed as blending agents for motor fuels or as solvents for lacquers, perfumes, and the like. They can be converted to halides, or ethers, or nitrated for the production of Diesel fuel ignition promoters. They may also be halogenated, oxidized, hydrogenated, dehydrogenated or dehydrated; the latter operation producing conjugated diolefins as previously mentioned.

EXAMPLE I

A 1-liter autoclave equipped with stirring means was charged with 16 g of 95.4% paraformaldehyde (0.509 mol), 200 ml of benzene, 1.0 g of finely ground iodine on alumina (0.9% by wt. I) and 308 g (5.500 mol) of isobutylene. The reaction mixture was heated for 1 hour at 200°C while the pressure (autogeneous) dropped from 1800 to 1725 psig. The reactor was cooled and the unreacted isobutylene (235 g) collected by distillation into an evacuated bomb. Analysis of the recovered isobutylene indicated that it contained only 0.02 wt. percent isoprene (0.05 g). The liquid material from the reaction vessel was filtered into a distilling flask and fractionally distilled into four fractions including the flask residue. The fractions were analyzed by gas-liquid chromatography (GLC) procedures. The analysis indicated a total of 19.45 g (0.226 mol) of 3-methyl-3-buten-1-ol and 4.26 g of the formate ester of the above alkenol. Based on the formaldehyde starting material, the yield of the alkenol was 44 percent.

The iodine on alumina catalyst was prepared by adding a solution of 1 g of $I_2$ in 250 ml of benzene to 50 g of Catapal alumina in the form of 1/16 inch extrudate. The mixture was allowed to stand at room temperature in a closed vessel. The supernatant liquid was decanted and the alumina washed with 150 ml of benzene. The alumina was then dried in a rotary evaporator at 100°C for 20 minutes. Analysis of the alumina thus treated gave an iodine content of 0.90 percent by weight.

EXAMPLE II

A series of four runs was conducted according to the instant invention in which iodine was employed as the catalyst for the reaction of formaldehyde and isobutylene in benzene diluent. The reactor charging procedure was essentially the same for each of the runs. A 1-liter autoclave equipped with stirring means was charged with 16 g of 94.4% paraformaldehyde (0.503 mol), 200 ml of benzene, iodine catalyst, and isobutylene. The reaction mixture was heated for 1 hour at the indicated temperature under autogeneous pressure. The reaction mixture was cooled and the products recovered as indicated below. The results of the runs are summarized below in Table I.

TABLE I

| Run No. | $I_2$, g | Isobutylene, g (mol) | Temp., °C | Isoprene, g (%) | Product, Yield Alkenol, g (%) | Formate, g |
|---|---|---|---|---|---|---|
| 1[a] | 0.5 | 295 (5.265) | 150 | —[b] | 6.64 (15) | —[c] |
| 2[d] | 0.5 | 290 (5.179) | 200 | —[b] | 14.85 (34) | —[b] |
| 3[e] | 0.2 | 285 (5.089) | 200 | —[b] | 9.21 (22) | 2.54 |
| 4[f] | 0.2 | 298 (5.321) | 200 | 5.88 (17) | 18.40 (42) | —[c] |

[a]At the end of the reaction period the autoclave was cooled, vented, and the reaction mixture washed with 20 ml of saturated aqueous NaHSO₃, then with 20 ml of water. The organic phase was dried over anhydrous Na₂SO₄, filtered, and then distilled into two fractions. Considerable unreacted formaldehyde was noted in the reaction mixture but the amount was not measured.
[b]Present in the distillate but the amount not measured.
[c]Not found by GLC analysis.
[d]At the end of the reaction period the autoclave was cooled, vented, and the contents filtered into a distillation flask. The product was distilled into four fractions which were analyzed by GLC. Isoprene was apparently formed during distillation.
[e]At the end of the reaction period the autoclave was cooled, vented, and the reaction mixture washed with 20 ml of saturated aqueous NaHSO₃, and then filtered into a distillation flask. The filtrate was distilled into four fractions which were analyzed by GLC.
[f]At the end of the reaction period, the unreacted isobutylene was recovered (310.3 g) in an evacuated bomb. Analysis of the recovered isobutylene for isoprene content indicated only 0.08% by weight of isoprene (0.25 g). The remaining reaction mixture was filtered into a distillation flask and distilled into two fractions which were analyzed by GLC.

EXAMPLE III

Other runs were conducted employing iodine as catalyst for the reaction of formaldehyde with isobutylene in benzene diluent. The reaction conditions employed in these runs are summarized in Table II and the results obtained are given in Table III.

TABLE II

| Run No. | $I_2$, g | Temp., °C | $CH_2O$,[a] g (mol) | Isobutylene, g (mol) | Benzene ml | Time, Hrs. |
|---|---|---|---|---|---|---|
| 1[b] | 0.2 | ~25 | 3.1 (0.1) | 23.7 (0.424) | 100 | 24 |
| 2[c] | 2 | 150 | 124 (3.936) | 255 (4.56) | 250 | 6 |
| 3[c] | 1 | 100 | 62 (1.968) | 260 (4.64) | 250 | 6 |
| 4[c] | 1 | 150 | 62 (1.968) | 263 (4.70) | 250 | 6 |

[a]95.2% paraformaldehyde.
[b]Reaction conducted in a glass bottle reactor under autogeneous pressure at room temperature.
[c]Reaction conducted in a one-liter autoclave under autogeneous pressure.

TABLE III

| Run No. | Approximate Wt. % by GLC Analysis of Reaction Mixture | | | |
|---|---|---|---|---|
| | Isoprene | Alkenol | Dioxane[a] | Other |
| 1 | No evidence of reaction by GLC | | | |
| 2 | Fractionally distilled but not analyzed | | | |
| 3[b] | None detected | 2.7 | 2.5 | (c) |
| 4[d] | 6.2 | 1.9 | 8.3 | (e) |

[a]4,4-Dimethyl-1,3-dioxane.
[b]At the end of the reaction period, the autoclave was cooled, vented, and the residue (300 g) analyzed.
[c]Isobutylene 13.2, methanol trace, and benzene 81.6. A large amount of unreacted formaldehyde was detected but not measured.
[d]At the end of the reaction period the autoclave was cooled, vented, and the residue (468 g) washed with saturated aqueous NaHSO₃, then with water and then dried over anhydrous Na₂SO₄.
[e]Isobutylene 22.9, methanol 6.5, benzene 52.0, unidentified product "A" 0.5, unidentified product "B" 1.2, and unidentified product "C" 0.6.

EXAMPLE IV

Runs were conducted which employed iodine as catalyst for the reaction of formaldehyde with isobutylene in the presence of aromatic ether diluents. Each run employed a 1-liter autoclave as the reaction vessel. In each run the reactor was charged with 16 g of 94.4% paraformaldehyde (0.503 mol), 200 ml of the aromatic ether, 0.2 g iodine, and the indicated amount of isobutylene. Each reaction mixture was heated under autogeneous pressure for 1 hour at 200°C except Run 4 which was heated 0.5 hour at 275°C. The results obtained in these runs are presented below in Table IV.

TABLE IV

| Run No. | Diluent | Isobutylene, g (mol) | Isoprene, g (%) | Alkenol, g (%) | Formate, g |
|---|---|---|---|---|---|
| 1[a] | Anisole | 310 (5.536) | 3.57 (10) | 19.21 (44) | —[b] |
| 2[c] | Diphenyl ether | 279 (4.982) | 9.81 (29) | 7.59 (18) | 0.25 |
| 3[d] | Diphenyl ether | 260 (4.643) | 18.64 (54) | 1.48 (3) | —[b] |
| 4[e] | Diphenyl | 302 (5.393) | 4.59 (13) | —[b] | —[b] |

[a]At the end of the reaction period the autoclave was cooled and the unreacted isobutylene (265 g) was recovered in an evacuated bomb. Analysis of the recovered isobutylene for isoprene showed an isoprene content of 0.03% by wt. (0.08 g). The liquid reaction mixture was washed with a Na₂S₂O₃ solution (5 g in 75 ml H₂O), then with a saturated Na₂CO₃ solution, then with water, and dried over MgSO₄. The reaction mixture was filtered, then distilled into five fractions for analysis by GLC.
[b]Not detected by GLC.

TABLE IV-continued (c) At the end of the reaction period the autoclave was cooled, vented, and the contents transferred to a separatory funnel for successive washings with an $Na_2S_2O_3$ aqueous solution, $Na_2CO_3$ aqueous solution, and water. The organic phase was filtered through anhydrous $Na_2SO_4$ to remove water. The filtrate was distilled into six fractions which were analyzed by GLC.
(d) At the end of the reaction period the autoclave was cooled, and the unreacted isobutylene (214.3 g) recovered in an evacuated bomb. Analysis of the recovered isobutylene for isoprene content showed an isoprene content of 0.40 wt. % (0.86 g). The liquid reaction mixture was filtered into a distillation flask and distilled into two fractions for analysis by GLC.
(e) At the end of the reaction period the autoclave was cooled and the unreacted isobutylene (257 g) recovered in an evacuated bomb. Analysis of the recovered isobutylene showed an isoprene content of 0.02 percent by weight (0.05 g). The liquid reaction mixture was filtered into a distillation flask and distilled into four fractions which were analyzed by GLC. A complex unidentified mixture of compounds (about 60 g) was also produced in this run.

EXAMPLE V (Control)

Other runs were made employing iodine as the catalyst for the reaction of formaldehyde and isobutylene in the presence of tetrahydrofuran (THF) as the diluent. The conditions employed in these runs are summarized in Table V and the results shown in Table VI.

TABLE V

| Run No. | $I_2$, g | THF, ml | $CH_2O$, g (mol) | Isobutylene, g (mol) | Temp., °C | Time, Hrs. |
|---|---|---|---|---|---|---|
| 1(a) | 2 | 100 | 12.6 (0.4)(b) | 28.4 (0.508)(c) | ~25 | 192 |
| 2(d) | 2 | 150 | 47.4 (1.5)(b) | 290 (5.18) | 150 | 6 |
| 3(d) | 0.5 | 200 | 16 (0.503)(c) | 282 (5.036) | 200 | 1 |

(a) Reaction conducted in a glass bottle reactor under autogeneous pressure at room temperature.
(b) 95.2% paraformaldehyde.
(c) 94.4% paraformaldehyde.
(d) Reaction conducted in a one-liter autoclave under autogeneous pressure.
(e) Reactor vented and recharged with 29.1 g isobutylene after two days.

TABLE VI

| Run No. | Approximate Wt. Percent by GLC Analysis | | | |
|---|---|---|---|---|
| | Isoprene | Alkenol | Dioxane(a) | Other |
| 1 | four unidentified compounds in small amounts | | | |
| 2(b) | 2.2 | 7.5 | 5.5 | (c) |
| 3(d) | (e) | trace | (e) | — |

(a) 4,4-Dimethyl-1,3-dioxane.
(b) After the reaction period the autoclave was cooled, vented, and the resulting mixture (250.6 g) analyzed by GLC.
(c) Isobutylene 20.5, THF 56.3, unidentified product "A" 1.5, unidentified product "B" 1.8, unidentified product "C" 1.9, and unidentified product "D" 3.1.
(d) After the reaction period the autoclave was cooled, vented, and the reaction mixture transferred to a separatory funnel where it was washed with saturated aqueous $NaHSO_3$, and then with water and then dried over anhydrous $MgSO_4$. The mixture was then fractionally distilled into four fractions which were analyzed by GLC.
(e) Not detected.

EXAMPLE VI (Control)

A 1-liter autoclave was charged with 200 ml of sulfolane, 0.5 g iodine, 16 g of 94.4% paraformaldehyde (0.503 mol), and 305 g (5.446 mol) of isobutylene. The reaction mixture was heated at 200°C for 1 hour while the pressure (autogeneous) decreased from 1000 to 800 psig. At the end of the reaction period the reactor was cooled and the unreacted isobutylene (117.6 g) recovered in a cooled evacuated bomb. The remaining reaction mixture which had separated into two layers was filtered into a distillation flask and 250 ml benzene added. Two layers still remained after the benzene was added. The mixture was distilled into six fractions and the two lower boiling fractions analyzed by GLC. No isoprene or 3-methyl-3-buten-1-ol was detected in said two fractions. However, diisobutylene (96.1 g) was found for a yield of 51 percent based on the starting isobutylene. Conversion of isobutylene was 61 percent in this run.

EXAMPLE VII (Control)

A 1-liter autoclave was charged with 16 g of 94.4% paraformaldehyde (0.503 mol), 0.5 g of iodine, 289 g (5.161 mol) of isobutylene, and 150 ml methanol. The reaction mixture was heated at 200°C for 1 hour. At the end of the reaction period the reactor was cooled, vented, and the mixture stirred for 1 hour with $NaHSO_3$ (1 g). The reaction mixture was filtered into a distilling flask and distilled into four fractions which were analyzed by GLC. No isoprene or 3-methyl-3-buten-1-ol were found in the fractions but a considerable amount of methyl t-butyl ether was found in the reaction mixture.

EXAMPLE VIII (Control)

A 1-liter autoclave was charged with 22 g of 94.4% paraformaldehyde (0.692 mol), 200 ml acetonitrile, 0.5 g iodine, and 295 g (5.268 mol) of isobutylene. The reaction mixture was heated 1 hour at 200°C while the pressure (autogeneous) dropped from 1500–1300 psig. At the end of the reaction period the reactor was cooled, vented, and the contents dissolved in diethyl ether. The ether solution was washed with 20% aqueous $Na_2S_2O_3$ solution, then with water, dried over anhydrous $MgSO_4$, and filtered into a distillation flask where the ether was stripped off. The residue was distilled into three fractions. Isoprene and 3-methyl-3-buten-1-ol were not detected in the fractions.

EXAMPLE IX (Control)

A 1-liter autoclave was charged with 53 g (0.5 mol) of benzaldehyde, 200 ml benzene, 0.5 g iodine, and 205 g (3.661 mol) of isobutylene. The mixture was heated for 4 hours at 200°C under autogeneous pressure. The reactor was cooled, vented, and reactor contents washed with aqueous $Na_2S_2O_3$, with water, aqueous $Na_2CO_3$, again with water and then dried over anhydrous $Na_2SO_4$. The mixture was filtered and the fractionally fractional distilled into two portions. Analysis of the product fractions indicated that the benzaldehyde did not react with isobutylene under the conditions employed.

EXAMPLE X (Control)

A 1-liter flask equipped with stirring means and a reflux condenser was charged with 56 g (0.5 mol) of 1-octene, 22 g of 94.4% paraformaldehyde (0.692 mol), 200 ml cyclohexane, and 10 ml of 47% HI. The reaction mixture was refluxed gently for 6 hours. the reaction mixture which contained much unreacted formaldehyde was washed with water, aqueous $Na_2S_2O_3$, aqueous $Na_2CO_3$, water again, and then dried over anhydrous $Na_2SO_4$. The mixture was filtered and the filtrate distilled. Only a trace of material boiling higher than 1-octene was obtained, indicating that 1-octene was essentially unreactive under the conditions employed.

EXAMPLE XI

A 1-liter autoclave was charged with 16 g of 94.4% paraformaldehyde (0.503 mol), 0.2 ml (0.47 g) bromine, 200 ml diphenyl ether, and 300 g (5.357 mol) isobutylene. The reaction mixture was heated for 1 hour at 200°C while the pressure (autogeneous) dropped from 950 to 900 psig. At the end of the reaction period the reactor was cooled and the unreacted isobutylene (237.5 g) recovered in an evacuated bomb. Analysis of the recovered isobutylene for isoprene content indicated 0.25% isoprene (0.59 g). The remaining reaction mixture was diluted with benzene, washed with aqueous $Na_2CO_3$, dried over anhydrous $MgSO_4$ and filtered. The filtrate was fractionally distilled into six fractions and the fractions analyzed by GLC. Analysis showed that 4.64 g (0.068 mol) of isoprene was obtained for a yield of 14 percent based on the starting formaldehyde. The analysis also showed that 15.42 g (0.179 mol) of 3-methyl-3-buten-1-ol was obtained for a yield of 36 percent based on the starting formaldehyde.

EXAMPLE XII

A 1-liter autoclave was charged with 16 g of 94.4% paraformaldehyde (0.503 mol), 200 ml benzene, 0.5 g iodine, 1.0 g potassium iodide, and 278 g (4.964 mol) of isobutylene. The reaction mixture was heated for 1 hour at 200°C while the pressure (autogeneous) dropped from 1000 to 850 psig. The reactor was cooled, vented, and the contents stirred with 1 g of $NaHSO_3$ fr for 1 hour at room temperature. The mixture was filtered into a distillation flask. The filtrate was fractionally distilled into four fractions which were analyzed by GLC. Each fraction contained isoprene but the amount was not measured. It is believed that the isoprene was formed during distillation of the product mixture. Analysis of the fractions showed that 7.27 g (0.084 mol) of 3-methyl-3-buten-1-ol had been obtained for a yield of 17 percent based on the starting formaldehyde. There was also obtained 3.13 g of the formate ester of the above alkenol.

EXAMPLE XIII

A series of runs was carried out employing 0.5 g of various metal iodides as catalysts for the reaction of formaldehyde, 16 g of 94.4% paraformaldehyde (0.503 mol), with isobutylene in the presence of 200 ml benzene. Each reaction was conducted in a 1-liter autoclave by heating the reaction mixture for 1 hour at 200°C under autogeneous pressure. At the end of each reaction period the reactor was cooled, vented and the contents filtered into a distillation flask for fractional distillation and analysis of the fractions by GLC. The results of these runs are shown in Table VII below.

Table VII

| Run No. | Catalyst | Isobutylene, g (mol) | Isoprene, g (%) | Product Yield Alkenol,[a] g (%) | Formate,[b] g |
|---|---|---|---|---|---|
| 1 | KI | 290 (5.179) | —[c] | 26.41 (61) | 1.01 |
| 2 | $CdI_2$ | 282 (5.036) | 1.29 (4) | 20.43 (47) | 1.91 |
| 3 | $NiI_2$ | 278 (4.964) | 4.34 (13) | 13.63 (32) | 3.30 |
| 4 | LiI | 290 (5.179) | 2.16 (6) | 7.84 (18) | —[c] |

[a]3-Methyl-3-buten-1-ol.
[b]Formate ester of (a) above.
[c]Not detected.

EXAMPLE XIV

A run was carried out to demonstrate the effectiveness of iodine in diphenyl ether as a dehydration agent for 3-methyl-3-buten-1-ol to produce iosprene. A 500 ml flask was charged with 200 ml diphenyl ether, 0.2 g iodine, and 43 g (0.50 mol) of 3-methyl-3-buten-1-ol. The flask was equipped with heating means, a distillation column, and cooled receiving vessel. The mixture was heated to distill the products and/or reactants. There was obtained 44.5 g of distillate including 8.0 g water. The organic layer of the product was composed of isoprene 30.16 g (0.44 mol), 3-methyl-3-buten-1-ol 5.47 g (0.064 mol), 3-methyl-2-buten-1-ol 0.15 g (0.002 mol), and trace amounts of other unidentified compounds. The results thus show a batch yield of isoprene of 89 percent and a conversion of 87 percent of the starting alkenol for an ultimate yield of essentially 100 percent isoprene based on the converted alkenol.

I claim:
1. A process for the production of alkenols or cycloalkenols which comprises reacting
   a. at least one olefinic compound selected from the group consisting of alkenes and cycloalkenes having from 3 to 20 carbon atoms per molecule and at least one allylic hydrogen with
   b. formaldehyde in the presence of
   c. a reaction diluent comprising aromatic compounds of the formula $Ar(Z)_n$ wherein Ar is an aromatic hydrocarbyl radical whose valence is $n$, $n$ is 0, 1, or 2, and wherein Z is a substituent selected from the group consisting of Cl— and R—O—, and where R is a hydrocarbyl radical of 1-10 carbon atoms, and
   d. a catalyst selected from the group consisting of

4. A process according to claim 1 for the production of 3-methyl-3-buten-1-ol which comprises reacting (a) isobutylene with (b) formaldehyde at a temperature in the range of about 150° to about 250°C under autogeneous pressure in the presence of (c) benzene, diphenyl ether, or anisole, and (d) a catalyst selected from the group consisting of bromine, iodine, potassium iodide and lithium iodide.

5. A process according to claim 1 for the production of 3-methyl-3-buten-1-ol which comprises reacting (a) isobutylene with (b) formaldehyde at a temperature in the range of about 150° to about 250°C under autogeneous pressure in the presence of (c) diphenyl ether, and (d) bromine as catalyst.

6. A process according to claim 1 wherein the catalyst is selected from the group consisting of bromine, iodine, potassium iodide and lithium iodide.

7. A process according to claim 1 wherein (c) is benzene, diphenyl ether, or anisole.

8. A process according to claim 1 for producing 3-methyl-3-buten-1-ol which comprises reacting (a) isobutylene with (b) formaldehyde in the presence of (c) diphenyl ether, and (d) iodine as catalyst.

9. A process for the production of alkenols or cycloalkenols which comprises reacting
   a. at least one olefinic compound selected from the group consisting of alkenes and cycloalkenes having from 3 to 20 carbon atoms per molecule and at least one allylic hydrogen with
   b. formaldehyde in the presence of
   c. a reaction diluent comprising aromatic compounds of the formula $Ar(Z)_n$ wherein Ar is an aromatic hydrocarbyl radical whose valence is $n$, $n$ is 0, 1, or 2, and wherein Z is a substituent selected from the group consisting of Cl— and R—O—, and where R is a hydrocarbyl radical of 1–10 carbon atoms, and
   d. a catalyst selected from the group consisting of bromine, metal bromides of Group IA metals, iodine, and metal iodides of Group IA metals, supported on a member selected from the group consisting of alumina, silica, silica-alumina, clays, carbon, and pumice, at an elevated temperature and pressure sufficient to produce alkenols or cycloalkenols.

2. A process according to claim 1 wherein said reacting is carried out at a temperature in the range of from about 50° to about 300°C and under autogeneous pressure with an amount of catalyst ranging from 0.01 to 20 weight percent based on the weight of formaldehyde present and a molar ratio of (a) to (b) in the range of 1:1 to 20:1.

3. A process according to claim 1 for the production of 3-methyl-3-buten-1-ol which comprises reacting isobutylene with formaldehyde in benzene reaction diluent containing an iodine-alumina catalyst.

hydrocarbyl radical whose valence is $n$, $n$ is 0, 1, or 2, and wherein Z is a substituent selected from the group consisting of Cl— and R—O—, and where R is a hydrocarbyl radical of 1–10 carbon atoms, and d. a catalyst selected from the group consisting of bromine, metal bromides of Group IA metals, iodine, and metal iodides of Group IA metals at an elevated temperature and pressure sufficient to produce alkenols or cycloalkenols.

10. A process according to claim 9 wherein said reacting is carried out at a temperature in the range of from about 50° to about 300°C and under autogeneous pressure with an amount of catalyst ranging from 0.01 to 20 weight percent based on the weight of formaldehyde present and a molar ratio of (a) to (b) in the range of 1:1 to 20:1.

11. A process according to claim 9 wherein (c) is benzene, diphenyl ether, or anisole.

12. A process according to claim 9 wherein the catalyst is selected from the group consisting of bromine, iodine, potassium iodide, and lithium iodide.

13. A process according to claim 9 wherein (c) is diphenyl ether and the catalyst is iodine.

14. A process according to claim 10 for producing 3-methyl-3-buten-1-ol which comprises reacting (a) isobutylene with (b) formaldehyde in the presence of (c) diphenyl ether, and (d) iodine as catalyst.

15. A process according to claim 10 wherein the catalyst is selected from the group consisting of iodine and a Group IA metal iodide.

* * * * *

UNITED STATES PATENT OFFICE
CERTIFICATE OF CORRECTION

Patent No. 3,956,407  Dated May 11, 1976

Inventor(s) Paul R. Stapp  Page 1 of 2

It is certified that error appears in the above-identified patent and that said Letters Patent are hereby corrected as shown below:

Column 10, line 68, after "of" insert -- hydrocarbyl radical whose valence is n, n is 0, 1, or 2, and wherein Z is a substituent selected from the group consisting of Cl- and R-O-, and where R is a hydrocarbyl radical of 1-10 carbon atoms, and d. a catalyst selected from the group consisting of bromine, metal bromides of Group IA metals, iodine, and metal iodides of Group IA metals at an elevated temperature and pressure sufficient to produce alkenols or cycloalkenols. --.

Column 11, delete lines 33 to 39, as insert instead -- bromine, metal bromides of Group IA metals, iodine, and metal iodies of Group IA metals, supported on a member selected from the group consisting of alumina, silica, silica-alumina, clays, carbon, and pumice, at an elevated temperature and pressure sufficient to produce alkenols or cycloalk- enols. --.

UNITED STATES PATENT OFFICE
CERTIFICATE OF CORRECTION

Patent No. 3,956,407    Dated May 11, 1976

Inventor(s) Paul R. Stapp    Page 2 of 2

It is certified that error appears in the above-identified patent and that said Letters Patent are hereby corrected as shown below:

Column 12, delete lines 10 thru 18.

Signed and Sealed this

Second Day of November 1976

[SEAL]

Attest:

RUTH C. MASON
*Attesting Officer*

C. MARSHALL DANN
*Commissioner of Patents and Trademarks*